United States Patent [19]

Kalthoff

[11] Patent Number: 5,084,935
[45] Date of Patent: Feb. 4, 1992

[54] MULTIPLE-PURPOSE WIRE SHAPING AND CUTTING TOOL

[75] Inventor: Ferdinand Kalthoff, Laer, Fed. Rep. of Germany

[73] Assignee: Orbis-Werk Groten GmbH & Co. KG, Ahaus, Fed. Rep. of Germany

[21] Appl. No.: 645,594

[22] Filed: Jan. 24, 1991

[30] Foreign Application Priority Data

Feb. 27, 1990 [DE] Fed. Rep. of Germany ....... 4006111

[51] Int. Cl.$^5$ .................................................. B25B 7/22
[52] U.S. Cl. .......................................... 7/132; 433/4; 140/106; 72/409
[58] Field of Search ................... 7/125, 127, 129, 130, 7/131, 132, 133, 134; 72/409; 140/106, 121, 123; 433/4

[56] References Cited

U.S. PATENT DOCUMENTS

| | | | |
|---|---|---|---|
| 515,799 | 3/1894 | Smith | 140/106 |
| 594,225 | 11/1897 | Berridge | 140/106 |
| 1,103,606 | 7/1914 | Montag | 433/4 |
| 1,887,732 | 11/1932 | Pagel et al. | 72/409 |
| 3,727,316 | 4/1973 | Goldberg | 433/4 |
| 3,804,132 | 4/1974 | Mann | 433/4 |
| 4,104,752 | 8/1978 | Amrein | 7/107 |
| 4,337,542 | 7/1982 | Theiler | 7/107 |

Primary Examiner—Roscoe V. Parker
Attorney, Agent, or Firm—Peter K. Kontler

[57] ABSTRACT

A multiple-purpose wire shaping and cutting tool wherein the two levers are connected to each other by a pivot between the jaws and the handles. The confronting sides of the handles are formed with complementary elongated male and female corrugating elements which extend radially of the pivot axis, and one of the handles has a wireholding hook-shaped member and a disc-shaped guide with a grooved peripheral surface for a length of wire. The other handle has a hole which is parallel to the pivot axis and registers with a socket of the guide member when the jaws of the two levers are adjacent each other. One of the jaws has a female bending portion with a groove extending in parallelism with the pivot axis, and the other jaw has a male bending portion with a rib which is received in the groove, with a certain amount of play, when the jaws are adjacent each other. The one jaw is further formed with a circumferentially complete groove, with an abutment and with a channel, and the other jaw has a corrugated guide portion and an anvil at the free end. The free ends of the jaws have confronting recesses extending radially of the pivot axis.

20 Claims, 3 Drawing Sheets

FIG.1

MULTIPLE-PURPOSE WIRE SHAPING AND CUTTING TOOL

BACKGROUND OF THE INVENTION

The invention relates to improvements in plier-shaped tools in general, and more particularly to improvements in multiple-purpose plier-shaped tools. Still more particularly, the invention relates to improvements in multiple-purpose tools which can be used with advantage for the shaping and severing or trimming of strip-shaped and/or wire-like products (hereinafter called wires for short).

U.S. Pat. No. 4,337,542 to Theier discloses a terminal crimping tool which can be utilized for manipulation of electrical connectors and terminals. The patented tool can be used as a means for stripping insulating sheaths off wire-like conductors having different diameters as well as to sever wire-like conductors. In addition, the patented tool can be used to crimp end portions of wire-like conductors and/or to form eyelets of different diameters. One lever of the tool is provided with a transversely extending groove which is parallel to the axis of the pivot member for the two levers, and the other lever has a transversely extending projection which can enter, with a certain amount of clearance, the groove in response to pivoting of the jaws of the two levers toward each other. The projection cooperates with the surface which surrounds the groove in order to shape a selected portion of an electric conductor.

A somewhat similar multiple-purpose tool is disclosed in U.S. Pat. No. 4,104,752 to Amrein et al. The two halves or levers of the tool are pivotally connected to each other and are provided with complementary insulation-stripping portions as well as with cutting edges for pieces of wire or the like. Still further, the two halves of the patented tool are provided with reaming devices as well as with complementary contouring portions. The tool of Amrein et al. also comprises a projection which extends in parallelism with the pivot axis, and a complementary groove which can receive the projection with a certain amount of clearance.

A drawback of presently known multiple-purpose tools is their lack of versatility and inability to carry out certain types of work. By way of example, orthodontists and makers of dental prostheses must shape different types of wire in a number of specific ways in order to impart to the wire a configuration which is needed in a brace or in another mechanical aid. These specialists are compelled to operate with a variety of different plier-shaped tools in order to carry out a series of successive operations upon a particular length of wire. As a rule, an orthodontist or a maker of dental prostheses will utilize at least three discrete types of plier-shaped tools, namely side nippers (which are used exclusively to sever pieces of wire), holding tools and shaping or forming tools. A holding tool serves to grasp a piece of wire in order to facilitate and simplify a bending or a like operation, for example, around a conical or cylindrical jaw of the holding tool. A shaping or forming tool is designed to engage a piece of wire at more than two discrete points and to impart to the wire a corrugated, zig-zag or like configuration as a result of movement of the jaws toward each other.

It will be seen that, at least in the field of orthodontics and dental prosthetics, there exists an urgent need for a tool which can perform a number of different operations in any desired sequence in order to save time as well as to avoid repeated switching from one tool to another.

OBJECTS OF THE INVENTION

An object of the invention is to provide a multiple-purpose tool which can be utilized for the shaping and/or other treatment of wire and is more versatile than heretofore known tools.

Another object of the invention is to provide a plier-shaped multiple-purpose tool which can be used with particular advantage by the makers, repairers and installers of tooth braces, dental prostheses and similar mechanical aids.

A further object of the invention is to provide a novel and improved tool which can carry out wire shaping, wire trimming and wire holding operations in any desired sequence.

An additional object of the invention is to provide a tool which can be used as a superior substitute for sets of heretofore used wire manipulating and cutting or trimming tools.

Still another object of the invention is to provide a novel and improved tool which can serve, among other purposes, as a simple, compact and inexpensive but efficient implement for the making of retentions, so-called Adams, U-shaped loops, labial bows and analogous components for use in the mouth of a person.

A further object of the invention is to provide a novel and improved method of making retentions, Adams, labial bows and analogous components.

SUMMARY OF THE INVENTION

The invention resides in the provision of a plier-shaped multiple-purpose tool for the treatment of wire and like bendable products, particularly for use by dentists (this term is intended to embrace dental technicians with all kinds of specializations including makers of braces and prostheses, doctors of dentistry and any other persons involved with the treatment and/or replacement of teeth). The improved tool comprises first and second elongated two-armed levers respectively having first and second handles or handgrip portions and first and second jaws, and a pivot which connects the levers to each other intermediate the handles and the respective jaws for movement—about an axis which extends transversely of the levers—between first positions in which the jaws and the handles are respectively adjacent each other and second positions in which the jaws and the handles are respectively remote from one another. The jaws have cooperating cutting edges which sever a wire, a strip or a like product in response to movement of the levers toward their first positions, one of the levers has a plurality of female corrugating elements, and the other of the levers has a plurality of male corrugating elements each of which is receivable with clearance in a discrete female corrugating element in response to movement of the levers to the first positions. In accordance with a feature of the invention, the male and female corrugating elements extend substantially radially of the axis which is defined by the pivot for the two levers.

The cutting edges preferably also extend substantially radially of the pivot axis, and the male and female corrugating elements can be provided on the handles of the respective levers. The arrangement is preferably such that the female corrugating elements have grooves and concave surfaces which bound the grooves, and that the male corrugating elements have or constitute ribs (which are substantially complementary to the grooves) and convex surfaces bounding the ribs.

One of the handles can further comprise a hook-shaped or similar wire holding member which is adjacent the pivot and projects from the respective lever in substantial parallelism with the pivot axis. The one handle preferably further comprises a substantially disc-shaped guide which is adjacent the holding member and has a grooved peripheral surface for reception of a length of wire. The other handle can be provided with a hole or bore which is adjacent and substantially parallel to the pivot axis. The hole has a closed (or closeable or sealable) first end and a substantially funnel-shaped wire-admitting second end. An end face of the disc-shaped guide can be provided with a socket which registers with one end of the hole in the first positions of the levers.

One of the jaws can be provided with a female wire bending portion, and the other jaw can comprise a complementary male wire bending portion which is received, with at least some clearance, in the female bending portion in response to movement of the levers to their first positions. The male and female bending portions are or can be at least substantially parallel to the pivot axis. The female bending portion has a groove and a concave surface bounding the groove, and the male bending portion has a rib and a convex surface bounding the rib. The one jaw can be further provided with an elongated abutment for wire, and such abutment is preferably parallel to and adjacent the groove of the female bending portion. Still further, the one jaw can comprise a wire-shaping and/or positioning shoulder which is adjacent the female bending portion and extends transversely of the respective lever and transversely of the pivot axis. The one jaw can also be provided with a circumferentially complete groove; the female bending portion is preferably disposed between the circumferentially complete groove and the pivot. The other jaw comprises a free end portion which is remote from the pivot and is provided with an anvil, and such other jaw can be provided with a substantially wedge-like (e.g., substantially pyramidal) intermediate portion which is disposed between the free end portion and the male bending portion and tapers toward the anvil. The other jaw can further comprise a corrugated guide portion between the male bending portion and the intermediate portion.

Those (free) end portions of the jaws which are remote from the pivot are or can be provided with confronting recesses which extend substantially radially of the pivot axis.

One of the jaws can include a cone which tapers in a direction away from the pivot, and the recess in the free end portion of the other jaw can be dimensioned to receive a portion (particularly the smaller-diameter end) of the cone.

One of the jaws is preferably provided with a roughened (e.g., serrated) inner side facing the other jaw.

One of the jaws can be provided with a channel having a first portion extending substantially radially of the pivot axis and facing the other jaw in the first positions of the levers. The channel preferably further comprises a substantially funnel-shaped second portion which is remote from the first portion and can diverge toward the respective free end as well as toward the pivot, and a third portion which connects the first and second portions and is or can be substantially normal to the pivot axis.

The novel features which are considered as characteristic of the invention are set forth in particular in the appended claims. The improved multiple-purpose tool itself, however, both as to its construction and its mode of operation, together with additional features and advantages thereof, will be best understood upon perusal of the following detailed description of certain presently preferred specific embodiments with reference to the accompanying drawing.

BRIEF DESCRIPTION OF THE DRAWING

FIG. 4b is a perspective view of the once deformed piece of wire of FIG. 4a;

FIG. 5 is a perspective view of a substantially U-shaped loop which can be formed by resorting to the plier-shaped multiple-purpose tool of FIGS. 1 to 3a; and FIG. 6 is a perspective view of a labial bow which can be formed by resorting to the tool of FIGS. 1 to 3a.

DESCRIPTION OF PREFERRED EMBODIMENTS

The plier-shaped tool which is shown in FIGS. 1, 2, 3, 3a and 3b comprises two crossing halves or levers 1, 2 and a pivot 5 serving to articulately connect the levers to each other so that the two handles 3, 4 are located at one side and the two jaws 1, 20 are located at the other side of the pivot axis. The pivot axis extends transversely of the levers 1, 2 and enables these levers to pivot between first positions (not shown) in which the free ends of the jaws 10, 20 are adjacent each other and the free ends of the handles 3, 4 are also adjacent each other, and second positions (shown in FIGS. 1 and 2) in which the two jaws as well as the two handles make relatively large acute angles.

Figures 1, 3, 3B:
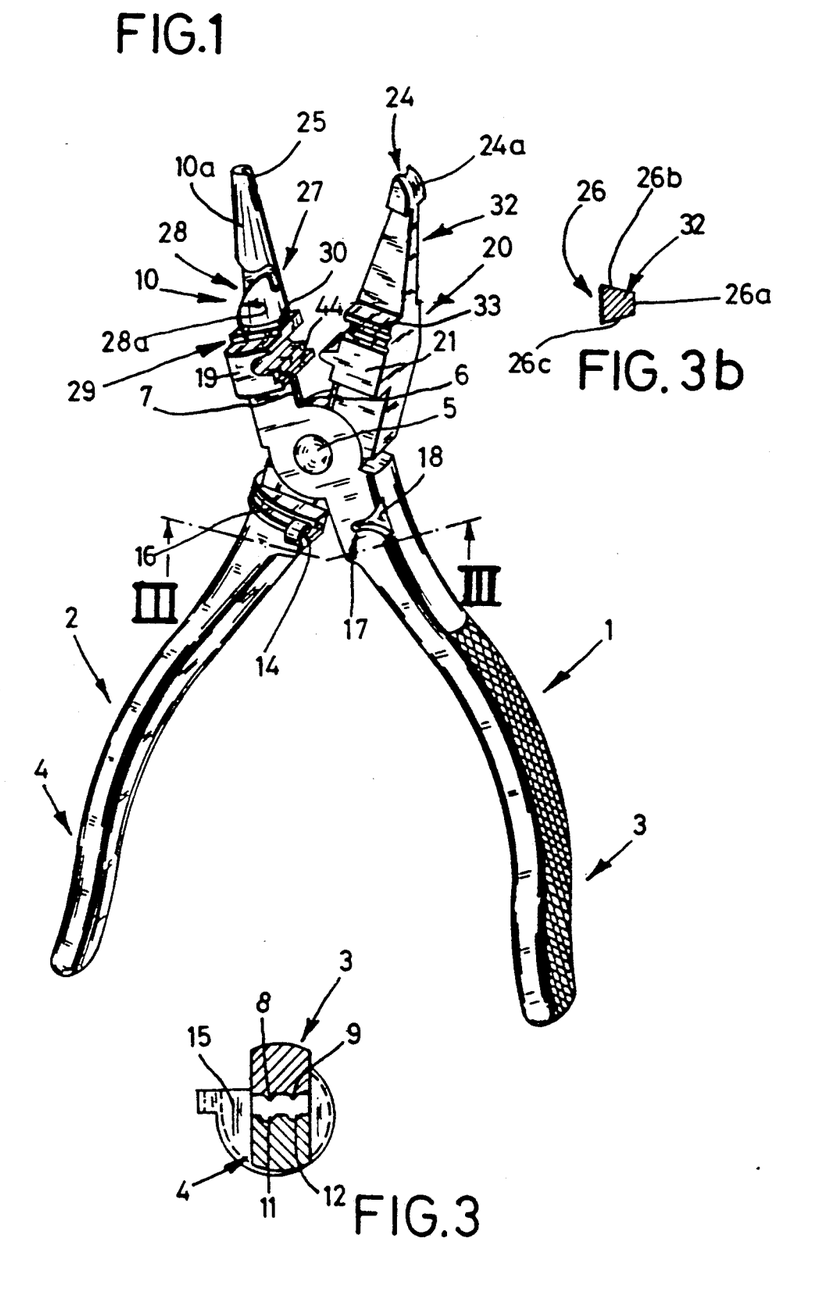
FIG. 1 is a perspective view of one side of a plier-shaped multiple-purpose tool which embodies one form of the invention, the two levers being shown in their second positions.
FIG. 3 is a transverse sectional view of the legs of the two levers, substantially as seen in the direction of arrows from the line III—III in FIG. 1.
FIG. 3b is a transverse sectional view of a wedge-like intermediate portion of one of the jaws.
Figures 2, 3A:
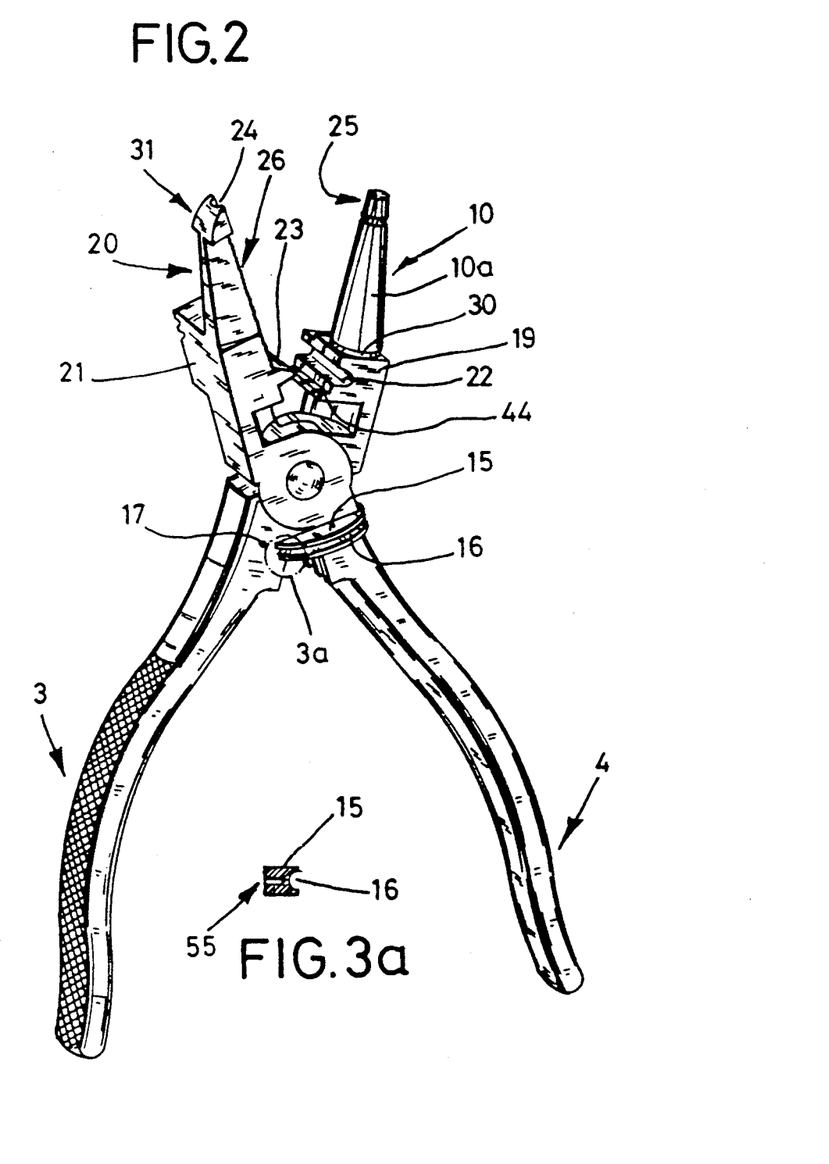
FIG. 2 is a perspective view of the other side of the tool which is shown in FIG. 1.
FIG. 3a is a transverse sectional view of a detail within the phantom-line circle 3a in FIG. 2.

That (inner) portion of the jaw 10 which is nearest to the pivot 5 is provided with a cutting edge 7 which extends radially of the pivot axis, the same as a cutting edge 6 which is provided on the adjacent inner portion of the jaw 20. The cutting edges 6, 7 can cooperate to trim pieces of wire, strips or like articles or blanks preparatory to or during shaping. The cutting edges 6, 7 can be said to constitute a so-called side clipper; these cutting edges are adjacent one side of the tool, i.e., nearer to one end than to the other end of the pivot 5.

Those portions of the handles 3, 4 which are adjacent the pivot 5 are provided with male corrugating elements 8, 9 (FIG. 3) which form part of the handle 3 and complementary female corrugating elements 11, 12 (FIG. 3) which form part of the handle 4. In accordance with a feature of the invention, the elongated rib-shaped male corrugating elements 8, 9 extend substantially radially of the axis which is defined by the pivot 5, and the same holds true for the elongated grooves of the female corrugating elements 11 and 12. The ribs of the male corrugating elements 8, 9 are bounded by convex surfaces, and the grooves of the female corrugating elements 11, 12 are bounded by complementary concave surfaces. The dimensions of the ribs and grooves are such that the male corrugating elements 8, 9 are received in the respective female corrugating elements 11, 12 with a certain amount of clearance when the levers 1, 2 are moved to their first positions in which the free ends of the jaws 10, 20 are immediately adjacent each other. The corrugating elements 8, 9 and 11, 12 can be put to use for the making of retentions such as those shown at 35 in FIGS. 5 and 6. The retentions facilitate the mounting of a removable partial denture in the mouth of a patient but can also serve many other useful purposes. The clearances between the male and female corrugating elements 8, 9 and 11, 12 provide room for the piece or pieces of wire which are to be converted into retentions or into similar configurations.

One side of the handle 4 is provided with a substantially hook-shaped or U-shaped wire holding member 14 which extends from the handle 4 adjacent and in parallelism with the pivot axis. The holding member 14 is or can be integral with the adjacent substantially radially extending end portion of a disc-shaped guide 15 surrounding a large part of the handle 4 adjacent the pivot 5 and having a peripheral surface 16 provided with an arcuate groove for a length of wire. The guide 15 extends well beyond the sides of the handle 4 as well as beyond the sides of the adjacent portion of the handle 3 (as seen in the axial direction of the pivot 5). The groove in the peripheral surface 16 of the guide 15 can receive a length of wire during the making of a labial bow 37 of the type shown in FIG. 6. More specifically, the guide 15 and the groove of its peripheral surface 16 can be put to use for the making of the arcuate portion 50 of the labial bow 37.

The handle 3 is formed with a hole or bore 17 which is substantially or exactly parallel to the axis of the pivot 5 and is adjacent the two ends of the guide 15. When the levers 1, 2 are moved to their first positions (in which the free ends of the jaws 10, 20 are immediately adjacent each other), one end of the guide 15 preferably closes or seals the adjacent end (shown in FIG. 2) of the hole 17 in the handle 3. The other end 18 of the hole 17 constitutes an enlarged funnel-shaped wire-admitting inlet. The non-enlarged end of the hole 17 registers with a blind hole or another suitable socket 55 (FIG. 3a) which is provided in the respective end face of the guide 15 so that the socket 55 can receive the very end of a length of wire which has been introduced by way of the funnel-shaped inlet 18 and has been advanced all the way through and beyond the hole 17. If the levers 1 and 2 are moved to the second positions (shown in FIGS. 1 and 2) subsequent to insertion of the tip of a length of wire into the socket 55 by way of the inlet 18 and the remaining portion of the hole 17, the resulting shearing effect ensures that the tip of the wire remains in the socket 55 and the adjacent portion of the wire remains in the hole 17. The hole 17 is sufficiently close to the pivot 5 to ensure that the wire which has been caused to pass through this hole and into the socket 55 does not interfere with manipulation of the handles 3, 4 for the purpose of pivoting the levers 1, 2 between their first (closed) and second (open) positions.

The jaw 10 is provided with a female wire bending portion 19 which has an elongated groove 22 extending transversely of the lever 1 and in at least substantial parallelism with the axis of the pivot 5. This groove can receive, with certain clearance, an elongated rib 23 forming part of a male bending portion 21 which, in turn, is an integral part of the jaw 20. The groove 22 of the female bending portion 19 is outwardly adjacent an elongated abutment 44 of the jaw 10; this abutment is parallel to the pivot axis and is disposed between the pivot 5 and the groove 22. The rib 23 is bounded by a substantially convex surface, and the groove 22 is bounded by a substantially concave surface. The clearance between the two surfaces (when the free ends of the jaws 10, 20 are immediately adjacent each other) suffices to permit insertion and desirable deformation as well as retention of a piece of wire which is to be shaped, e.g., in a manner to be described with reference to FIGS. 4a–4f, 5 and 6.

The outer side of the female bending portion 19 (namely that side which does not face the jaw 20) is provided with a wire shaping shoulder 29 which, in turn, is adjacent a circumferentially complete groove 30 in the peripheral surface of a conical portion 10a of the jaw 10. The conical portion 10a tapers in a direction away from the pivot 5, i.e., toward the free end of the jaw 10. The circumferentially complete groove 30 is provided in the maximum-diameter portion or base of the conical portion 10a.

The surface of the conical portion 10a (hereinafter called cone) is formed with a channel 27 having a first portion facing the jaw 20 and extending substantially radially of the pivot axis, a funnel-shaped second portion 28 which faces away from the jaw 20, and a third portion which connects the first and second portions and extends substantially transversely of the pivot axis. The funnel-shaped portion 28 of the channel 27 is bounded by two convex surfaces 28a which can be used to bend a portion of wire extending into the channel 27.

The male bending portion 21 of the jaw 20 is inwardly adjacent a grooved or corrugated guide portion 33 of the jaw 20; the corrugations of the guide portion 33 are disposed at one side of the jaw 20 and extend transversely of the pivot axis and transversely of the respective lever 2 at that side of the lever 2 which is provided with the wire holding member 14. A substantially wedge-like intermediate portion 32 (see also FIG. 3b) of the jaw 20 is disposed between the male bending portion 21 and an anvil 31 at the free end of the jaw 20. The intermediate portion 32 has a substantially trapeziform cross-sectional outline (FIG. 3b) and its cross-sectional area decreases in a direction from the bending portion 21 toward the anvil 31. The inner side of the intermediate portion 32 is roughened (e.g., serrated), as at 26, and faces the jaw 10. The width of the roughened inner side 26 exceeds the width of the outer side 26a of the intermediate portion 32 of the jaw 20 (as measured in the direction of the axis of the pivot 5). The trapeziform cross-sectional outline of the intermediate portion 32 of the jaw 20 renders it possible to grip a portion of a wire between the roughened inner side 26 and the cone 10a (in the first positions of the levers 1, 2) and to deform the wire circumferentially around the portion 32 so that the wire portion which extends transversely of the inner side 26 and the adjacent wire portion adjacent the lateral surface 26b or 26c of the portion 32 make an angle of less than 90°.

The outer side 24a of the anvil 31 at the free end of the jaw 20 is bounded by a convex surface, and the inner side of the free end of the jaw 20 is formed with a recess 24 which extends radially of the pivot axis and can receive, in part, the free (smaller-diameter) end of the cone 10a. The free end of the cone 10a has a recess 25 which extends radially of the pivot axis and is received in the recess 24 in the first positions of the levers 1 and 2.

Figure 4A:
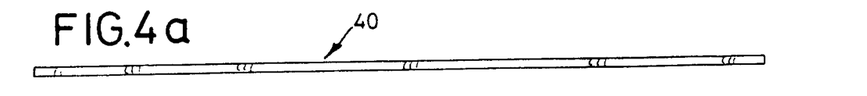
FIG. 4a shows a straight piece of wire which can be manipulated by the tool of FIGS. 1 to 4.
Figure 4B:
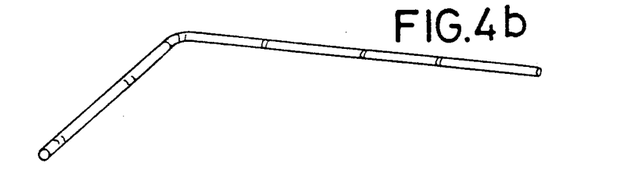
Figure 4C:
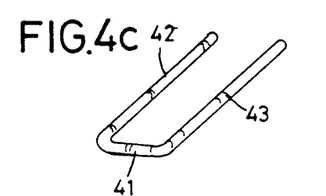
FIG. 4c is a perspective view of the wire subsequent to conversion into a substantially U-shaped body.
Figure 4D:
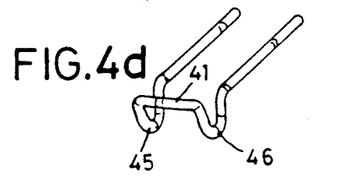
FIG. 4d is a perspective view of the U-shaped body subsequent to the formation of teeth in its legs close to the web.
Figure 4E:
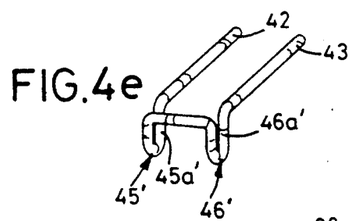
FIG. 4e is a perspective view of the body of FIG. 4d subsequent to deformation of the two teeth.
Figure 4F:
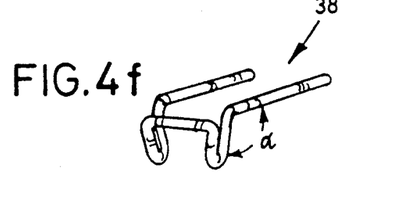
FIG. 4f is a perspective view of the body of FIG. 4e which constitutes a so-called Adams and is obtained as a result of completion of at least one additional deforming step.
Figure 5:
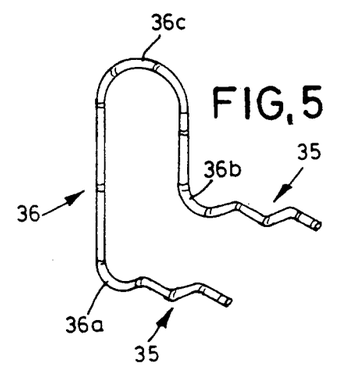
Figure 6:
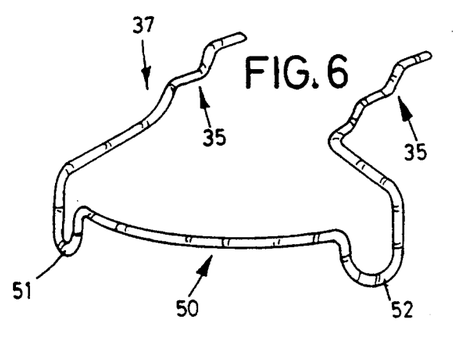

The improved plier-shaped multiple-purpose tool can be used in a number of different ways, for example, for the making of an Adams 38 of the type shown in FIG. 4f, for the making of a U-loop 36 of the type shown in FIG. 5, or for the making of a labial bow 37 of the type shown in FIG. 6.

In order to provide a piece of wire with a retention 35, a portion of the wire is caused to enter the gap between the handles 3, 4 in the second positions of the levers 1, 2 (as actually shown in FIGS. 1, 2 and 3) so that the selected portion of the wire extends in parallelism with the pivot axis between the (still spaced apart) male corrugating elements 8, 9 and female corrugating elements 11, 12. The free ends of the handles 3, 4 are then caused to move toward each other so that the ribs of the male corrugating elements 8, 9 enter the grooves of the respective female corrugating elements 11, 12 whereby the thus deformed portion of wire assumes the shape as shown at 35 in FIGS. 5 and 6. Retentions 35 are desirable and advantageous when smooth-surfaced end portions of a piece of round wire are to be reliably anchored in a plastic material. The thus obtained article can constitute a yoke, brace or arch. Each of the two end portions of the U-loop 36 of FIG. 5 and each of the two end portions of the bow 37 of FIG. 6 can be corrugated (to constitute a retention 35) in a separate step.

The Adams 38 which is shown in FIG. 4f can be formed in the following way:

One starts with an elongated smooth-surfaced piece 40 of wire which is shown in FIG. 4a. A median portion of the piece 40 is placed against the roughened inner side 26 of the jaw 20 so that it extends in parallelism with the axis of the pivot 5. The wire is then grasped between the inner side 26 and the cone 10a and is bent along one edge of the inner side 26 and toward the lateral surface 26b or 26c. If the bent portion of the wire is moved all the way into contact with the lateral surface 26b or 26c, the thus obtained sections of the originally straight portion 40 make an angle of at least slightly less than 90°. Bending through an angle of more than 90° is desirable and advantageous because this accounts for elasticity of the material of the wire. The resulting V-shaped or L-shaped piece of wire is shown in FIG. 4b. The bend between the two sections of the V-shaped or L-shaped intermediate product is off center if the next step involves the making of a U-shaped body of the type shown in FIG. 4c. Such body is obtained in the same way as described in connection with conversion of the straight piece 40 into the V-shaped or L-shaped structure of FIG. 4b, i.e., the structure of FIG. 4b is clamped between the inner side 26 of the jaw 20 and the cone 10a of the jaw 10 and is bent against the lateral surface 26b or 26c to convert the structure of FIG. 4b into a U-shaped body having two substantially parallel legs 42, 43 and a web 41. If the length of the leg 42 and/or 43 is excessive, the respective leg is shortened by the trimming or severing device including the cutting edges 6 and 7.

The next step involves placing the U-shaped body of FIG. 4c between the jaws 10, 20 in such a way that the web 41 is adjacent and parallel to the axis of the pivot 5. The legs 42, 43 extend outwardly across the space between the bending portions 19 and 21, i.e., between the groove 22 and the rib 23 (while the jaws 10, 20 are held in the positions which are shown in FIGS. 1 and 2). Insertion of the U-shaped body is completed when the web 41 comes into contact with the abutment 44 which can be said to constitute a ledge extending in parallelism with the axis of the pivot 5. When the free ends of the handles 1, 2 are thereupon moved toward each other, the jaws 10, 20 also move their free ends toward each other and the rib 23 enters the groove 22 to provide the legs 42, 43 with substantially V-shaped or toothed projections 45, 46 which are adjacent the web 41 (see FIG. 4d).

In order to more reliably engage a tooth, the width of the open ends of the V-shaped projections 45, 46 should be reduced. This is achieved in the following way: The projection 45 is inserted into the channel 27 of the cone 10a and the free ends of the jaws 10, 20 are pivoted toward each other so that the projection 45 in the channel 27 is engaged and deformed by the roughened inner side 26 of the jaw 20. This results in conversion of the projection 45 into the modified V-shaped projection 45' of FIG. 4e. The projection 46 is thereupon converted into the modified projection 46' of FIG. 4e in the same way as described in connection with the projection 45.

In FIG. 4e, the angle between the remaining portion of the leg 42 and the adjacent portion 45a' of the projection 45' is greater than 90°. The same applies for the angle between the straight portion of the leg 43 and the adjacent portion 46a' of the projection 46'. However, these angles should be less than 90°, preferably close to or exactly 80° (the angle alpha which is shown in FIG. 4f is assumed to equal or approximate 80°). In other words, it is necessary to change the orientation of the projections 45', 46' relative to the straight portions of the respective legs 42, 43. To this end, the projection 45' and thereupon the projection 46' is retained in the channel 27 and the partially finished Adams is bent along the convex surface 28a in order to reduce the angle from more than 90° to approximately or exactly 80°. The finished Adams 38 is shown in FIG. 4f.

It is further desirable that the planes of the projections 45' 46' in the finished Adams 38 be slightly inclined relative to each other (as shown in FIG. 4f), i.e., that the apices of the projections 45', 46' be nearer to each other than the straight portions of the legs 42, 43. To this end, the projection 45' is inserted into the recesses 24 and 25 (prior or subsequent to a reduction of the angle alpha to 80°) and the straight portion of the leg 42 is bent along the convex surface 24a of the anvil 31. The projection 46' is thereupon inserted into the recesses 24, 25 and the straight portion of the leg 43 is bent along the convex surface 24a of the anvil or back support 31. This completes the conversion of the originally straight piece 40 of wire which is shown in FIG. 4a into the Adams 38 of FIG. 4f. If desired or necessary, the straight portions of the legs 42, 43 can be thereupon converted into or provided with retentions 35 by shaping the legs between the male corrugating elements 8, 9 and the female corrugating elements 11, 12 in a manner as described hereinbefore.

In order to convert an elongated piece 40 of wire into the U-loop 36 of FIG. 5, one end of the wire is inserted into the hole 17 by way of the enlarged funnel-shaped inlet 18. Such insertion takes place while the free ends of the handles 3, 4 are closely adjacent each other so that the disc-shaped guide 15 is immediately adjacent the other end of the hole 17 and such other end registers with the socket 55 in the guide 15. Thus, the inserted end of the wire can advance beyond the hole 17 and into the socket 55. That portion of the wire which is immediately adjacent the inlet 18 of the hole 17 is then bent transversely of the handle 3 to form a bend 36a at the inlet 18, and the wire is then bent into the groove of the peripheral surface 16 of the guide 15, either clockwise or counterclockwise, to form the respective portion of the U-loop 36 of FIG. 5. Bending of the wire at the inlet 18 of the hole 17 is facilitated by the funnel-shaped configuration of this inlet.

The next step of making the U-loop 36 includes inserting the other end of the wire into the hole 17 and into the registering socket 55. The free ends of the handles 3, 4 are then moved away from each other so that the inserted end of the wire is held in the hole 17 and in the socket 55 in response to development of a shearing effect. The person in charge then forms the bend 36b. The resulting (substantially twin V-shaped) intermediate product is then inserted into the corrugated guide portion 33 of the jaw 20 and is clamped in inserted position in response to pivoting of the free ends of the jaws 10 and 20 toward each other. The clamped portion of the wire then extends into the adjacent portion of the circumferentially complete groove 30 of the jaw 10 and can be provided with the centrally located bend 36c by flexing it around the maximum-diameter end of the cone 10a.

If necessary, the last step involves the making of retentions 35 by shaping the substantially or exactly straight ends of the U-loop 36 between the male corrugating elements 8, 9 and the respective female corrugating elements 11, 12.

In order to convert a piece 40 of wire into the labial bow 37 of FIG. 6, a substantially centrally located portion of the wire is inserted into the hook-shaped holding member 14 of the handle 4 and the tool is turned so that a portion of the wire which is adjacent the holding member 14 enters the groove in the peripheral surface 16 of the disc-shaped guide 15. This results in the making of the arcuate portion 50 which is shown in FIG. 6. The teeth 51 and 52 which flank the arcuate portion 50 are obtained by grasping the wire between the roughened inner side 26 of the intermediate portion 32 of the jaw 20 and the cone 10a of the jaw 10, and by thereupon bending the wire around the intermediate portion 32 and/or around the cone 10a in order to form teeth 51 and 52 of desired size and shape. The free ends of the thus obtained labial bow 37 are trimmed (if necessary) by the cutting edges 6 and 7. If necessary, the trimmed ends of the bow 37 are thereupon provided with retentions 35 by inserting the free ends between the male corrugating elements 8, 9 and female corrugating elements 11, 12 prior to moving the free ends of the handles 3, 4 toward each other.

The improved multiple-purpose tool can be used with equal or similar advantage for the making of other articles from pieces of wire or strip material. For example, the tool can be used for the making of so-called removable appliances with labial bows and frontal springs, frontal springs and so-called Jakel spreading clasps as well as Adamses and for activation of U-loops.

It will be seen that the improved tool renders it possible to carry out a number of successive or even simultaneous wire shaping and trimming operations. This simplifies the task of the user because her or his hands need not be accustomed to a plurality of different tools. Moreover, the conversion of blanks into finished articles in the form of loops, clasps, braces or the like can be completed within short intervals of time because the user need not repeatedly switch from tool to tool. The improved tool renders it possible to shape wire blanks or the like with a high degree of accuracy and reproducibility irrespective of whether certain portions of the blank must be converted into rounded, angular and/or otherwise configurated bodies. For example, a blank can be converted into a shaped article having one or more arcuate portions which are parts of circles, one or more V-shaped or L-shaped portions, one or more zig-zag shaped or otherwise corrugated or undulated portions, one or more looped portions and/or combinations of one or more partially straight and partially arched portions. At the same time, the tool renders it possible to trim the one or the other end of a fresh blank or the one or the other end of a partially converted blank at any stage of the shaping operation, i.e., prior to the first deforming step, between two successive deforming steps or upon completion of the last deforming step or steps. The various portions of the handles 3, 4 and jaws 10, 20 (such as the roughened inner side 26 in combination with the cone 10a) render it possible to reliably hold a wire-like blank against rotation in the course of a shaping operation. Furthermore the recesses 24, 25 and the convex surface 24a of the anvil 31 render it possible to change the orientation of neighboring portions of a partially deformed blank relative to each other, e.g., to change the mutual inclination of legs on a substantially U-shaped partially converted blank, to change the mutual inclination of a tooth-shaped or otherwise configurated projection and an adjacent straight portion of a partly converted blank and/or to compensate for elasticity of the material of a blank.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, the handle of one of said levers having a plurality of female corrugating elements and the handle of the other of said levers having a plurality of male corrugating elements each receivable with clearance in one of said female elements in response to movement of said levers to said first positions, said elements extending substantially radially of said axis.

2. The tool of claim 1, wherein said cutting edges extend substantially radially of said axis.

3. The tool of claim 1, wherein said female corrugating elements have grooves and concave surfaces bounding said grooves, said male corrugating elements having ribs substantially complementary to said grooves and convex surfaces bounding said ribs.

4. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female elements in response to movement of said levers to said first positions, said elements extending substantially radially of said axis and one of said handles comprising a wire holding member adjacent said pivot and projecting from the respective lever in substantially parallelism with said axis, said one handle further comprising a substantially disc-shaped guide adjacent said holding member and having a grooved peripheral surface.

5. The tool of claim 4, wherein said corrugating elements are provided on the handles of the respective levers.

6. The tool of claim 4, wherein the other of said handles has a hole which is adjacent and substantially parallel to said axis, said hole having a closed or closeable first end and a substantially funnel-shaped wire-admitting second end.

7. The tool of claim 6, wherein said guide has an end face provided with a socket which registers with one of said ends of said hole in the first positions of said levers.

8. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of sad levers having a plurality of female corrugating elements and the other of said levers having a plurality of male corrugating elements each receivable with clearance in one of said female corrugating elements in response to movement of said levers to said first positions, said elements extending substantially radially of said axis and one of said elements having a hole which is adjacent and substantially parallel to said axis, said hole having a closed or closable first end and a substantially funnel-shaped wire-admitting second end.

9. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female elements in response to movement of said levers to said first positions, said elements extending substantially radially of said axis and one of said jaws comprising a female wire bending portion, the other of said jaws comprising a complementary male wire bending portion which is received with clearance in said female portion in response to movement of said levers to said first positions and said bending portions being substantially parallel to said axis.

10. The tool of claim 9, wherein said female bending portion has a groove and a concave surface bounding said groove, said male bending portion having a rib and a convex surface bounding said rib.

11. The tool of claim 10, wherein said one jaw further comprises an elongated abutment which is parallel to and adjacent said groove.

12. The tool of claim 9, wherein said one jaw further comprises a wire-positioning shoulder adjacent said female bending portion and extending transversely of the respective lever and transversely of said axis.

13. The tool of claim 9, wherein said one jaw has a circumferentially complete groove, said female bending portion being disposed between said groove and said pivot.

14. The tool of claim 9, wherein said other jaw further comprises a free end remote from said pivot and provided with an anvil, and a substantially wedge-like intermediate portion disposed between said free end and said male bending portion and tapering toward said anvil.

15. The tool of claim 14, wherein said other jaw further comprises a corrugated guide portion between said male bending portion and said intermediate portion.

16. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female elements in response to movement of said levers to said first positions, said elements extending substantially radially of said axis and said jaws having free ends remote from said pivot and provided with confronting recesses extending substantially radially of said axis.

17. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female elements in response to movement of said levers to said first positions, said elements extending substantially radially of said axis and one of said jaws including a cone which tapers in a direction away from said pivot, said jaws having free ends remote from said pivot and the free end of the other of said jaws having a recess for a portion of said cone.

18. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female elements in response to movement of said levers to said first positions, said elements extending substantially radially of said axis and one of said jaws having a roughened inner side facing the other of said jaws.

19. A plier-shaped multiple-purpose wire treating tool, particularly or use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female elements in response to movement of said levers to said first positions, said elements extending substantially radially of said axis, one of said jaws having a channel having a first portion extending substantially radially of said axis and facing the other of said jaws in the first positions of said levers, said channel further having a substantially funnel-shaped second portion remote from said first portion and a third portion connecting said first and second portions.

20. A plier-shaped multiple-purpose wire treating tool, particularly for use by dentists, comprising first and second elongated levers respectively having first and second handles and first and second jaws; and a pivot connecting said levers to each other intermediate said handles and the respective jaws for movement, about an axis which extends transversely of said levers, between first positions in which said jaws and said handles are respectively adjacent each other and second positions in which said jaws and said handles are respectively remote from one another, said jaws having cooperating cutting edges which sever a wire in response to movement of said levers toward said first positions thereof, one of said levers having a plurality of female corrugating elements and the other of said levers having a plurality of male corrugating elements each receivable with clearance in one of said female corrugating elements in response to movement of said levers to said first positions, said elements extending substantially radially of said axis and said female corrugating elements having grooves and concave surfaces bounding said grooves, said male corrugating elements having ribs substantially complementary to said grooves and convex surfaces bounding said ribs.

* * * * *